US00PP35464P2

(12) United States Plant Patent
Koning

(10) Patent No.: US PP35,464 P2
(45) Date of Patent: Nov. 7, 2023

(54) ***LAVANDULA* PLANT NAMED 'ANOUK DELUXE 1802'**

(50) Latin Name: *Lavandula stoechas*
Varietal Denomination: Anouk Deluxe 1802

(71) Applicant: L. KONING BEHEER B.V., Nuis (NL)

(72) Inventor: Lammert Koning, Nuis (NL)

(73) Assignee: L. KONING BEHEER B.V., Nuis (NL)

( * ) Notice: Subject to any disclaimer, the term of this patent is extended or adjusted under 35 U.S.C. 154(b) by 0 days.

(21) Appl. No.: 18/115,691

(22) Filed: Feb. 28, 2023

(51) Int. Cl.
*A01H 5/02* (2018.01)
*A01H 6/50* (2018.01)

(52) U.S. Cl.
USPC ..... Plt./445

(58) Field of Classification Search
USPC ..... Plt./263.1, 445
See application file for complete search history.

*Primary Examiner* — Karen M Redden
(74) *Attorney, Agent, or Firm* — C. Anne Whealy

(57) ABSTRACT

A new and distinct cultivar of *Lavandula* plant named 'Anouk Deluxe 1802', characterized by its compact, upright and broadly spreading plant habit; freely branching growth habit; freely flowering habit; dark violet-colored flowers and bright purple-colored terminal flower bracts positioned on strong and erect peduncles; long flowering period; and good garden performance.

2 Drawing Sheets

Figure 1:
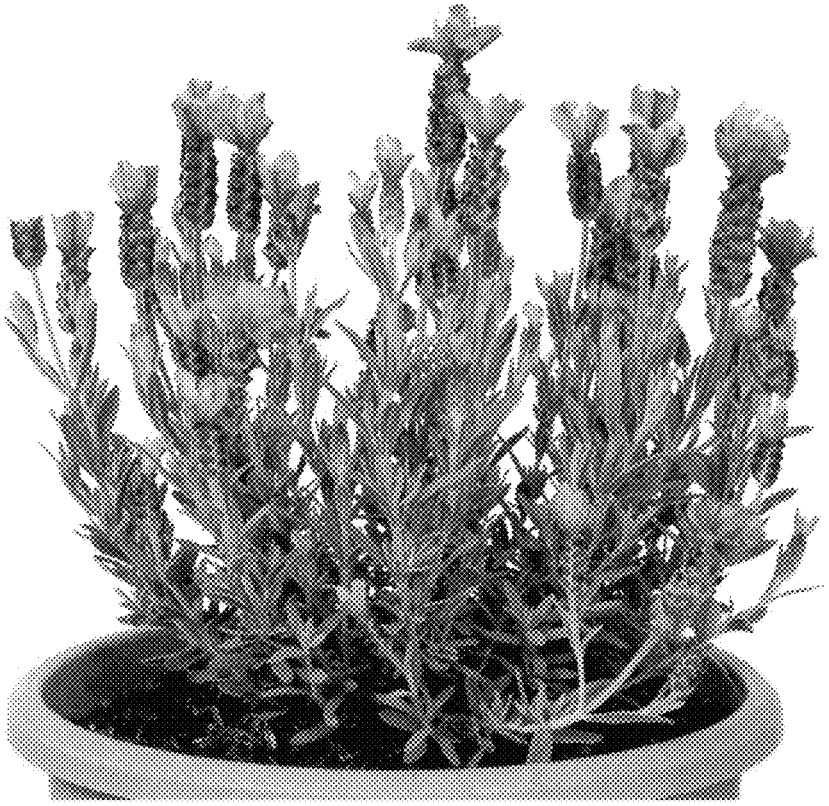

Botanical designation: *Lavandula stoechas.*
Cultivar denomination: 'ANOUK DELUXE 1802'.

STATEMENT REGARDING PRIOR DISCLOSURES BY APPLICANT

An European Plant Breeder's Rights application for the instant plant was filed by the Applicant on Jun. 30, 2022, application number 2022/1629. Foreign priority is not claimed to this application.

BACKGROUND OF THE INVENTION

The present invention relates to a new and distinct *Lavandula* plant, botanically known as *Lavandula stoechas*, commonly referred to as Lavender and hereinafter referred to by the name 'Anouk Deluxe 1802'.

The new *Lavandula* plant is a product of a planned breeding program conducted by the Inventor in Boskoop, The Netherlands. The objective of the breeding program was to develop new unique *Lavandula* plants with good performance and attractive plant form and flower coloration.

The new *Lavandula* plant originated from a cross-pollination in May, 2017 of *Lavandula stoechas* 'Anouk Deluxe 16115', disclosed in U.S. Plant Pat. No. 35,064, as the female, or seed, parent with *Lavandula stoechas* 'Anouk Deluxe 1642', not patented, as the male, or pollen, parent. The new *Lavandula* plant was discovered and selected by the Inventor as a single flowering plant within the progeny of the stated cross-pollination in a controlled environment in Boskoop, The Netherlands in July, 2018.

Asexual reproduction of the new *Lavandula* plant by terminal cuttings in a controlled greenhouse environment in Boskoop, The Netherlands since September, 2018 has shown that the unique features of this new *Lavandula* plant are stable and reproduced true to type in successive generations.

SUMMARY OF THE INVENTION

Plants of the new *Lavandula* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of the new *Lavandula* plant. These characteristics in combination distinguish 'Anouk Deluxe 1802' as a new and distinct *Lavandula* plant:

1. Compact, upright and broadly spreading plant habit.
2. Freely branching growth habit.
3. Freely flowering habit.
4. Dark violet-colored flowers and bright purple-colored terminal flower bracts positioned on strong and erect peduncles.
5. Long flowering period.
6. Good garden performance.

Plants of the new *Lavandula* differ primarily from plants of the female parent, 'Anouk Deluxe 16115', primarily in the following characteristics:

1. Plants of the new *Lavandula* are more compact than plants of 'Anouk Deluxe 16115'.
2. Plants of the new *Lavandula* have broader leaves than plants of 'Anouk Deluxe 16115'.
3. Plants of the new *Lavandula* have lighter purple-colored terminal flower bracts than plants of 'Anouk Deluxe 16115'.

Plants of the new *Lavandula* differ primarily from plants of the male parent, 'Anouk Deluxe 1642', primarily in the following characteristics:

1. Plants of the new *Lavandula* have slightly broader leaves than plants of 'Anouk Deluxe 1642'.

2. Plants of the new *Lavandula* have lighter purple-colored terminal flower bracts than plants of 'Anouk Deluxe 1642'.

Plants of the new *Lavandula* can be compared to plants of the *Lavandula stoechas* 'Anouk', disclosed in U.S. Plant Pat. No. 16,685. In side-by-side comparisons, plants of the new *Lavandula* differ primarily from plants of 'Anouk' in the following characteristics:

1. Plants of the new *Lavandula* are more compact than plants of 'Anouk'.
2. Leaves of plants of the new *Lavandula* are broader and more greyish green in color than leaves of plants of 'Anouk'.
3. Plants of the new *Lavandula* have brighter and darker purple-colored terminal flower bracts than plants of 'Anouk'.
4. Plants of the new *Lavandula* will rebloom whereas plants of 'Anouk Deluxe' rarely rebloom.

Plants of the new *Lavandula* can also be compared to plants of the *Lavandula stoechas* 'Toscane', disclosed in U.S. Plant Pat. No. 18,046. In side-by-side comparisons, plants of the new *Lavandula* differ primarily from plants of 'Toscane' in the following characteristics:

1. Plants of the new *Lavandula* are more compact than plants of 'Toscane'.
2. Leaves of plants of the new *Lavandula* are broader and more greyish green in color than leaves of plants of 'Toscane'.
3. Plants of the new *Lavandula* have brighter and darker purple-colored terminal flower bracts than plants of 'Toscane'.
4. Plants of the new *Lavandula* will rebloom whereas plants of 'Toscane' rarely rebloom.

BRIEF DESCRIPTION OF THE PHOTOGRAPHS

The accompanying photographs illustrate the overall appearance of the new *Lavandula* plant showing the colors as true as it is reasonably possible to obtain in colored reproductions of this type. Colors in the photographs may differ slightly from the color values cited in the detailed botanical description which accurately describe the colors of the new *Lavandula* plant.

The photograph on the first sheet (FIG. 1) is a side perspective view of a typical flowering plant of 'Anouk Deluxe 1802' grown in a container.

Figure 2:
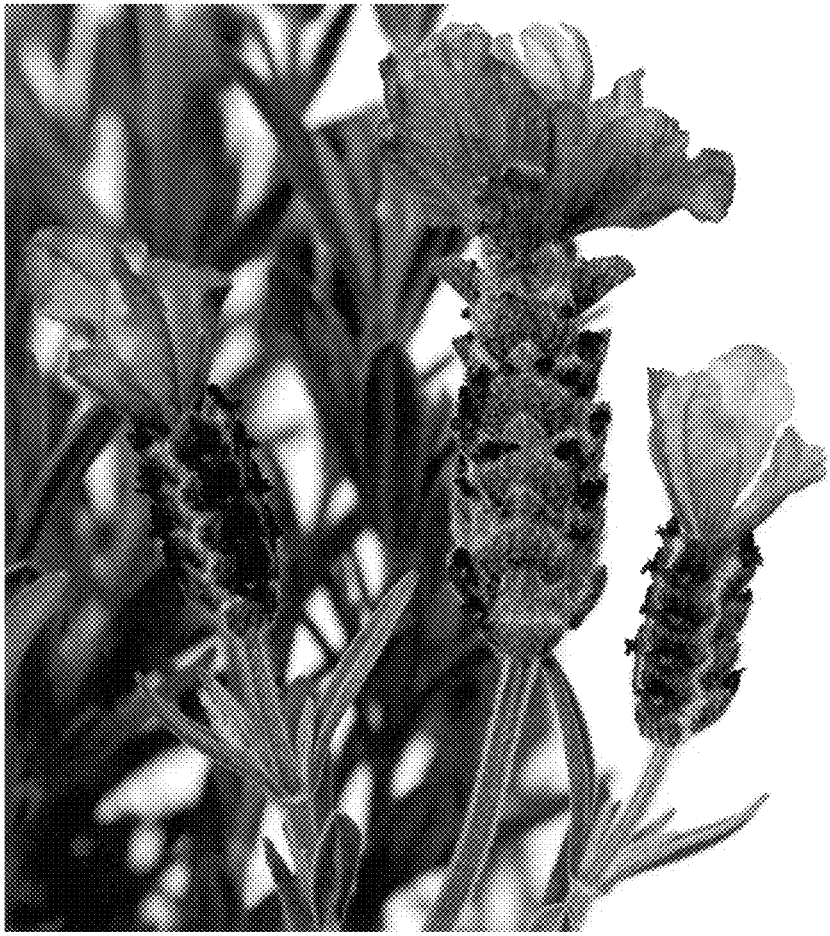

The photograph on the second sheet (FIG. 2) is a close-up view of a typical flowering plant of 'Anouk Deluxe 1802'.

DETAILED BOTANICAL DESCRIPTION

Plants used in the aforementioned photographs and following detailed description were grown in 25-cm containers during the spring and early summer in an outdoor nursery in Boskoop, The Netherlands and under cultural practices typical of commercial *Lavandula* production. Plants were pinched one time and were nine months old when the photographs and description were taken. During the production of the plants, day temperatures ranged from 10C to 30C and night temperatures ranged from 5C to 20C. In the following description, color references are made to The Royal Horticultural Society Colour Chart, 2015 Edition, except where general terms of ordinary dictionary significance are used.

Botanical classification: *Lavandula stoechas* 'Anouk Deluxe 1802'.

Parentage:

*Female, or seed, parent.*—*Lavandula stoechas* 'Anouk Deluxe 16115', disclosed in U.S. Plant Pat. No. 35,064.

*Male, or pollen, parent.*—*Lavandula stoechas* 'Anouk Deluxe 1642', not patented.

Propagation:

*Type*.—Terminal vegetative cuttings.

*Time to initiate roots, summer and winter*.—About ten days at temperatures about 18C.

*Time to produce a rooted young plant, summer*.—About 60 days at temperatures about 20C.

*Time to produce a rooted young plant, winter*.—About 70 days at temperatures about 20C.

*Root description*.—Fine, fibrous; initially white in color and becoming more brown with development; actual color of the roots is dependent on substrate composition, water quality, fertilizer type and formulation.

*Rooting habit*.—Freely branching; dense.

Plant description:

*Plant and growth habit*.—Herbaceous perennial; compact, upright and broadly spreading plant habit; flattened globular in overall plant shape; freely branching habit; moderately vigorous growth habit; moderate growth rate; flowers arranged in verticillasters on crowded spikes with showy terminal flower bracts.

*Plant height, soil level to top of foliar plane*.—About 18.8 cm.

*Plant height, soil level to top of floral plane*.—About 26.2 cm.

*Plant width*.—About 30.3 cm.

*Lateral branch description*.—Quantity per plant: About twelve primary lateral branches each with about three secondary lateral branches developing per plant; pinching enhances branching potential. Length: About 12.8 cm. Diameter: About 3 mm. Internode length: About 1.7 cm. Strength: Moderately strong. Aspect: Primary lateral branches, upright to about 40 degrees from vertical; secondary lateral branches, about 52.5 degrees from primary lateral branch axis. Texture and luster: Moderately to densely tomentose; matte. Color, when developing: Close to 145A. Color, developed: Close to 143B and 145A; with development, close to 199B, N199A and N199B.

*Leaf description*.—Arrangement: Opposite, simple; sessile. Length: About 3.4 cm. Width: About 8.5 mm. Shape: Narrowly oblong to narrowly oblanceolate. Apex: Broadly acute. Base: Cuneate. Margin: Entire; moderately revolute; not lobed. Texture and luster, upper surface: Densely tomentose; not rugose; matte. Texture and luster, lower surface: Densely tomentose; slightly rugose; matte. Fragrance: Strongly aromatic, pungent. Venation pattern: Pinnate. Color: Developing leaves, upper surface: Close to 138A. Developing leaves, lower surface: Close to NN137D. Fully expanded leaves, upper surface: Close to NN137C; venation, close to 145A. Fully expanded leaves, lower surface: Close to 146A; venation, close to 146D.

Flower description:

*Flower type, arrangement and habit*.—Small single salverform flowers arranged in compact verticillasters on crowded terminal spikes; freely flowering, about 120 flowers developing per inflorescence and about 6,000 flowers developing per plant; flowers with two-lobed upper lip and three-lobed lower lip; flowers face mostly outwardly on the spike; inflorescences with showy terminal flower bracts.

*Natural flowering season*.—Long flowering period; continuous from late spring into the summer in The Netherlands; plants reblooming for about ten weeks.

*Flower longevity on the plant*.—Individual flowers last about four weeks on the plant; flowers not persistent.

*Fragrance*.—None detected.

*Flower buds*.—Length: About 4.5 mm. Diameter: About 1.5 mm. Shape: Oblong. Texture and luster: Densely tomentose; matte. Color: Close to 143A; towards the base, close to 145B and at the apex, close to N77D.

*Inflorescence size*.—Height, including terminal flower bracts: About 5.7 cm. Height, excluding terminal flower bracts: About 3.6 cm. Diameter, at terminal flower bracts: About 3.1 cm. Diameter, below flower bracts: About 1.7 cm.

*Flower size*.—Diameter: About 3 mm by 3.5 mm. Depth (height): About 8 mm. Throat diameter: About 1 mm. Tube length: About 4.5 mm. Tube diameter: About 1.25 mm.

*Petals*.—Quantity and arrangement: Upper lip, two-lobed and lower lip, three-lobed. Length, upper lip: About 2 mm. Length, lower lip: About 1 mm. Width, upper lip: About 1.5 mm. Width, lower lip: About 1.25 mm. Shape: Roughly spatulate; lower 70% fused into a tube. Apex: Obtuse. Margin: Entire; moderately undulate. Texture and luster, upper surface: Smooth, glabrous; moderately velvety; not rugose; matte. Texture and luster, lower surface: Smooth, glabrous; slightly velvety; not rugose; matte. Texture, throat: Smooth, glabrous; slightly velvety. Texture, tube: Smooth, glabrous. Color: When opening, upper surface: Upper lip, close to N92A and lower lip, close to a blend of N92A and N92C. When opening, lower surface: Close to N92D. Fully opened, upper and lower surfaces: Close to N92D; venation, close to N92D; color does not change with subsequent development. Throat: Close to N92D; venation, close to N92D. Tube: Close to 86B fading proximally to close to NN155A; venation, close to 86B and NN155A.

*Terminal flower bracts*.—Quantity and arrangement: About 8 to 22 positioned mostly upright at inflorescence apex. Length: About 0.5 cm to 2.5 cm. Width: About 0.2 cm to 1.6 cm. Shape: Obovate to narrowly obovate. Apex: Obtuse to bluntly acute. Base: Acuminate. Margin: Entire; moderately to strongly undulate. Texture and luster, upper and lower surfaces: Moderately tomentose; matte. Color, upper surface: Close to N81B and N82D; midvein, close to 200A. Color, lower surface: Close to N81B and N82D; midvein, close to N77B.

*Basal flower bracts*.—Quantity and arrangement: Each group of seven flowers is subtended by a single basal flower bract. Length: About 9 mm. Width: About 9 mm. Shape: Broadly rhomboidal. Apex: Abruptly acute. Base: Acuminate. Margin: Ciliate. Texture and luster, upper surface: Moderately tomentose; slightly glossy. Texture and luster, lower surface: Moderately tomentose; matte. Color, upper surface: Close to N79D; venation, close to 146A. Color, lower surface: Close to 186B to 186C; venation, close to a blend of N186C and 200A.

*Sepals*.—Quantity and arrangement: Five, fused into a campanulate tube. Calyx length: About 4.5 mm. Calyx diameter: About 2 mm. Length: About 4.5 mm. Width: About 0.75 mm. Shape: Linear. Apex: Acute. Margin: Entire. Texture and luster, upper surface: Smooth, glabrous; glossy. Texture and luster, lower surface: Densely tomentose; slightly glossy. Color: When opening and fully opened, upper surface: Close to 145C and at the apex, close to N77D; venation, close to 145A. When opening and fully opened, lower surface: Close to 143A; towards the base, close to 145B and at the apex, close to N77D; venation, similar to lamina colors.

*Peduncles*.—Length: About 5.7 cm. Diameter: About 2 mm. Aspect: Mostly upright. Strength: Strong. Texture and luster: Densely tomentose; matte. Color: Close to 143B and 144B; distally, close to a blend of N186B and N186C.

*Reproductive organs*.—Stamens: Quantity per flower: Four. Filament length: About 1 mm. Filament color: Close to 85C. Anther shape: Short oblong; dorsifixed. Anther size: About 0.75 mm by 0.75 mm. Anther color: Close to 161D. Pollen amount: Scarce. Pollen color: Close to 16B. Pistils: Quantity per flower: One. Pistil length: About 2.75 mm. Stigma shape: Club-shaped. Stigma diameter: About 0.3 mm. Stigma color: Close to N186A. Style length: About 2.25 mm. Style color: Close to 157D. Ovary color: Close to 144A.

*Seeds and fruits*.—To date, seed and fruit production has not been observed on plants of the new *Lavandula*.

Pathogen & pest resistance: To date, plants of the new *Lavandula* have not been noted to be resistant to pathogens and pests common to *Lavandula* plants.

Garden performance: Plants of the new *Lavandula* have exhibited good tolerance to rain and wind and have been observed to tolerate temperatures from about 1C to about 40C and to be suitable for USDA Hardiness Zones 7 to 10.

It is claimed:

1. A new and distinct *Lavandula* plant named 'Anouk Deluxe 1802' as illustrated and described.

* * * * *